US006476201B1

United States Patent
Lowell et al.

(12)

(10) Patent No.: US 6,476,201 B1
(45) Date of Patent: Nov. 5, 2002

(54) METHODS FOR THE PRODUCTION OF NON-COVALENTLY COMPLEXED AND MULTIVALENT PROTEOSOME SUB-UNIT VACCINES

(75) Inventors: George H. Lowell, Hampstead (CA); Wendell D. Zollinger, Silver Spring; James F. Wood, Germantown, both of MD (US)

(73) Assignees: ID Biomedical Corporation of Quebec, Quebec (CA); The United States of America as represented by the Secretary of the Army, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/043,529
(22) PCT Filed: Sep. 18, 1996
(86) PCT No.: PCT/US96/15002
§ 371 (c)(1),
(2), (4) Date: Jul. 27, 1998
(87) PCT Pub. No.: WO97/10844
PCT Pub. Date: Mar. 27, 1997

Related U.S. Application Data

(60) Provisional application No. 60/003,859, filed on Sep. 18, 1995.

(51) Int. Cl.⁷ .................................................. A23J 1/00
(52) U.S. Cl. ...................... 530/414; 530/412; 530/350; 424/197.11; 424/203.1; 424/234.1; 424/249.1; 435/243; 435/101; 536/123.1
(58) Field of Search ......................... 424/197.11, 203.1, 424/234.1, 249.1; 530/350, 412, 414; 435/243, 101; 536/123.1

(56) References Cited

U.S. PATENT DOCUMENTS 5,102,989 A * 4/1992 Sitrin et al.
5,145,702 A * 9/1992 Sitrin et al.

OTHER PUBLICATIONS

Orr et al. Infection and Immunity. Nov. 1994. 62(11): 5198–5200.*
Orr et al. Infection and Immunity. Jun. 1993. 61(6): 2390–2395.*
Livingston et al. Vaccine. 1993. 11(12): 1199–1204.*

* cited by examiner

*Primary Examiner*—Jennifer E. Graser
(74) *Attorney, Agent, or Firm*—Morrison & Foerster LLP (57) ABSTRACT

A continuous method for preparing proteosome-amphiphilic determinant vaccines for parenteral or mucosal administration using diafiltration or ultrafiltration technology. The amphiphilic determinants include lipopolysaccharides from gram negative bacteria, e.g. *S. flexneri, P. shigelloides* and *S. sonnei*. Proteosomes are obtained from group B type 2b meningococci. The active proteosome-amphiphilic determinant complexes (non-covalent complexes) of the vaccine are formed using diafiltration or ultrafiltration to remove the detergent under non-static conditions. The use of diafiltration or ultrafiltration decreases processing time and the opportunity for contamination and further permits the use of ambient temperature and efficient scale-up. In addition, the process permits the reliable and continuous monitoring of the dialyzate which enhances the efficiency of the entire process. The time of dialysis for the production of a lot of vaccine is reduced from 7–10 days to less than 72 hours and usually less than 48 or 24 hours. The use of the process optimizes the presence of each antigenic component in the preparation of multivalent vaccines.

25 Claims, 7 Drawing Sheets

| Route & Dose | ASCs (Antibody Secreting Cells) (# cells / $10^6$ PBL)* | | | Fold Increase in ELISA Antibodies (Pre- / Post-Immunization) | | | | | | Responders in ASC or ELISA Antibody Assays (IgG, IgA or IgM) |
|---|---|---|---|---|---|---|---|---|---|---|
| | | | | Serum | | | Salivary | | Urinary | |
| | IgA | IgG | IgM | IgA | IgG | IgM | IgA | IgG | IgA | |
| Intranasal 1 mg | 9 | 2 | 12 | 4 | <2 | <2 | <2 | 2 | 6 | i.n. 1 mg |
| | 41 | 0 | 45 | 11 | 4 | 57 | 4 | 2 | 18 | ASC: 6/6 |
| | 4 | 1 | 67 | 10 | 4 | 12 | 2 | 2 | 2 | Serum: 6/6 |
| | 2 | 2 | 1 | 4 | 5 | <2 | 2 | 2 | 5 | Salivary: 3/6 |
| | 476 | 190 | 220 | 55 | 34 | 12 | 9 | 4 | 35 | Urinary: 5/6 |
| | 143 | 36 | 47 | 105 | 11 | 5 | 10 | 15 | 50 | Total: 6/6 |
| Responders**: | 4/6 | 4/6 | 5/6 | 6/6 | 5/6 | 4/6 | 3/6 | 2/6 | 5/6 | |
| Intranasal 0.4 mg | 1 | 2 | 3 | 3 | <2 | 2 | <2 | <2 | | i.n. 0.4 mg |
| | 0 | 0 | 7 | <2 | <2 | 2 | <2 | <2 | <2 | ASC: 5/6 |
| | 2 | 11 | 7 | <2 | 5 | 3 | 2 | 4 | <2 | Serum: 4/6 |
| | 18 | 6 | 57 | 7 | 6 | <2 | <2 | 3 | 6 | Salivary: 1/6 |
| | 3 | 0 | 1 | <2 | <2 | 6 | <2 | <2 | <2 | Urinary: 2/6 |
| | 24 | 8 | 30 | 4 | 4 | <2 | 2 | <2 | 5 | Total: 5/6 |
| Responders**: | 2/6 | 4/6 | 4/6 | 2/6 | 3/6 | 1/6 | 0/6 | 1/6 | 2/6 | |
| Intranasal 0.1 mg | 6 | 9 | 2 | <2 | 16 | | | | | i.n. 0.1 mg |
| | 0 | 0 | 11 | 3 | <2 | | | | | ASC: 3/6 |
| | 0 | 0 | 1 | <2 | <2 | | | | | Serum: 2/6 |
| | 20 | 18 | 42 | 5 | 3 | | | | | Salivary: |
| | 2 | 0 | 0 | <2 | <2 | | | | | Urinary: |
| | 1 | 0 | 1 | <2 | <2 | | | | | Total: 3/6 |
| Responders**: | 2/6 | 2/6 | 2/6 | 1/6 | 1/6 | | | | | |
| Oral 2 mg | 0 | 0 | 3 | <2 | <2 | 3 | <2 | | <2 | p.o. 2 mg |
| | 47 | 34 | 3 | 2 | <2 | <2 | <2 | | 7 | ASC: 3/6 |
| | 0 | 0 | 4 | <2 | <2 | <2 | <2 | | 4 | Serum: 0/6 |
| | 7 | 7 | 2 | <2 | <2 | <2 | <2 | | <2 | Salivary: 0/6 |
| | 3 | 0 | 3 | <2 | <2 | 3 | <2 | | 3 | Urinary: 2/6 |
| | 5 | 2 | 3 | <2 | <2 | <2 | <2 | | <2 | Total: 4/6 |
| Responders**: | 2/6 | 3/6 | 0/6 | 0/6 | 0/6 | 0/6 | 0/6 | | 2/6 | |
| Oral 0.5 mg | 5 | 2 | 0 | | | | | | | p.o. 0.5 mg |
| | 0 | 2 | 3 | | | | | | | ASC: 3/6 |
| | 5 | 1 | 3 | | | | | | | Serum: |
| | 2 | 0 | 3 | | | | | | | Salivary: |
| | 11 | 1 | 3 | | | | | | | Urinary: |
| | 0 | 0 | 0 | | | | | | | Total: 6/6 |
| Responders**: | 1/6 | 2/6 | 0/6 | | | | | | | |

\* ASC and serum ELISA values = peak responses after 1 or 2 immunizations (most values were after only 1 immunization)

\*\* ASC Responders with = or > 6, 2 or 5 ASCs per $10^6$ PBL for IgA, IgG and IgM, respectively (these values are 2 cells > mean no. whole cells + 3 S.D. of pre-immunization values of 30 volunteers)

\*\* Responders with = or > 4-fold increases in serum ELISA antibody levels post-immunization compared to pre-immunization

METHODS FOR THE PRODUCTION OF NON-COVALENTLY COMPLEXED AND MULTIVALENT PROTEOSOME SUB-UNIT VACCINES

This application is a national stage application of PCT application No. PCT/US96/15002, filed Sep. 18, 1996, which is based on provisional application No. 60/003,859, filed Sep. 18, 1995.

1. FIELD OF THE INVENTION

This invention concerns methods of production and compositions for non-covalently complexed multivalent proteosome vaccines for mucosal and parenteral administration.

2. BACKGROUND OF THE INVENTION

In order for multivalent sub-unit vaccines to stimulate optimal immune responses to each of the components, the proper components should be appropriately associated and each be available to the immune system so that they may be efficiently recognized and processed by cells of the immune system. Prime examples of such non-covalently complexed vaccines include proteosome vaccines which can consist of neisserial outer membrane protein proteosomes non-covalently complexed to a wide variety of antigens including peptides, lipopeptides, transmembrane or toxoided proteins, polysaccharides or lipopolysaccharides (LPS) (patent application Ser. No. 07/065,440 filed Jun. 23, 1987 "Immunogenic peptide vaccines and methods of preparation"; Ser. No. 07/336,952 filed Apr. 12, 1989 Immunopotentiaing system for large proteins and polypeptides"; Ser. No. 07-958,426 filed Oct. 8, 1992 "Oral or Intranasal Vaccines Using Hydrophobic Complexes Having Proteosomes and Lipopolysaccharides"; Ser. No. 08/029,666 filed Mar. 11, 1993 "Immunopotentiating Systems for Preparation of Immunogenic Materials"; Ser. No. 08/143,365 filed Oct. 29, 1993 "Immunopotentiating Systems for Preparation of Immunogenic Materials"; Ser. No. 93/10,402 filed Oct. 29, 1993 "Submicron Emulsions as Vaccine Adjuvants"; Ser. No. 08/063,613 filed May 18, 1994 Solid Fat Nanoemulsions as Vehicles for Vaccine Delivery" and publications Orr, N., Robin, G., Cohen, D., Arnon, R. and Lowell, G. H. (1993). Immunogenicity and Efficacy of Oral or Intranasal Shigella flexneri 2a and *Shigella sonnei* Proteosome-Lipopolysaccharide Vaccines in Animal Models. Infect. Immun. 61:2390; Mallett, C. P., T. L. Hale, R. Kaminski, T. Larsen, N. Orr, D. Cohen, and G. H. Lowell. 1995. Intranasal or intragastric immunization with proteosome-Shigella lipopolysaccharide vaccines protect against lethal pneumonia in a murine model of shigellosis. Infect. Immun. 63:2382–2386.; Lowell G H, Kaminski R W, Grate S et al. (1996) Intranasal and intramuscular proteosome-staphylococcal enterotoxin B (SEB) toxoid vaccines: immunogenicity and efficacy against lethal SEB intoxication in mice. Infec. Immun. 64:1706–1713.; Lowell, G. H. (1990) Proteosomes, Hydrophobic Anchors, Iscoms and Liposomes for Improved Presentation of Peptide and Protein Vaccines. in *New Generation Vaccines*: G. C. Woodrow and M. M. Levine, eds. (Marcel Dekker, NY). Chapter 12 (pp. 141–160) and Lowell, G. H., W. R. Ballou, L. F. Smith, R. A. Wirtz, W. D. Zollinger and W. T. Hockmeyer. 1988. Proteosome-lipopeptide vaccines: enhancement of immunogenicity for malaria CS peptides. Science 240:800.)

The contents of all the documents cited herein are expressly incorporated by reference.

For practical application in administering vaccines to protect against disease, it is frequently necessary to deliver several such antigens at the same time usually due to the fact that individuals are susceptible to the contraction of diseases caused by a variety of organisms. Moreover, several organisms, whether or not they are related to one another, often are endemic in the same location and therefore individuals requiring protection may need vaccination with several types of vaccines.

In the past, the production of vaccines that require non-covalent complexing of components has been accomplished using simple dialysis in which components are placed in dialysis tubing in the presence of dialyzable detergent and the mixture is dialyzed for 7–10 days to attempt to remove the detergent. The practical disadvantages of this system tend to severely preclude the advanced development and commercialization of this technology for several reasons including 1) Time: Length of time of the procedure: The need to use GMP resources for weeks while the vaccine is dialyzing is impractical both due to the excess costs involved and the increased opportunity for breakdown or contamination of mechanical or biological components during this extended period of time; 2) Contamination: Increased opportunity for contamination: dialysis tubing is difficult to sterilize, dialysis tubing requires manually opening and closing the system thereby exposing the components to contamination during both the loading and unloading process. Since many days transpire between loading and unloading the tubing, the risk of a small contamination in the initial days of the process may readily be magnified during the many days of dialysis to render this method useless for practical vaccine manufacture. The risk of puncturing the bag can result in loss of product. 3) Temperature: Necessity to perform the dialysis at 40° C. due to the extensive time involved; 4) Volume of dialyzing fluids: In order to manufacture vaccine for scale-up of the process, the use of massive amounts of dialysis fluid would be necessary since a 200:1 ratio of liquid outside to the dialysis tubing to inside the tubing is typically required. Therefore, for example, the production of a pilot lot of two liters of vaccine would require 400 liters of fluid outside the tubing per day—4,000 liters per 10 days—and the production of a production lot of 20–200 liters would require 40,000–4,000,000 liters. These amounts are wasteful and impractical compared to the method used in the instant invention; Dialysis tubing is not scalable since large amounts of product is problematic and 5) Inability to readily measure completeness of removal of the detergent so as to maximize vaccine effectiveness. Since the dialysis bag is placed in a container with 200 volumes of buffer, the ongoing measurement of detergent removal is neither practical nor feasible and 6) In addition, no method has been described for the measurement of the presence of the detergent used in the preferred embodiment, Empigen BB.

The second problem solved in this invention is the demonstration of the method of producing and delivering multivalent vaccines. Components can either be made together or produced separately and mixed together prior to administration. The instant invention demonstrates the optimal way of preparing such multivalent vaccines.

3. SUMMARY OF THE INVENTION

The subject of the instant invention broadly relates to the production and manufacture of proteosome-amphiphilic determinant vaccines designed for either parenteral or especially for mucosal administration including , but not limited to, respiratory (e.g. including intranasal, intrapharyngeaeal and intrapulmonary), gastro-intestinal (e.g. including oral or rectal) or topical (e.g. conjunctival or otic) administration to induce both systemic (serum) and mucosal (including respiratory and intestinal) antibody responses. An amphiphilic determinant is a molecule having hydrophobic and hydrophilic regions which, when appropriately formulated with proteosomes, align with the proteosomes to for a complex which elicits an immunologic response in a subject. Typical amphiphilic determinants include glycolipids, liposaccharides (including detoxified lipopolysaccharides), lipopeptides, transmembrane, envelope or toxoided proteins, or proteins or peptides with intrinsic hydrophobic amino acid anchors. These determinant materials can be obtained from gram negative bacteria including eschefichia, klebsiella, pseudomonas, *hemophilus brucella*, shigella and neisseria. More specifically, the invention relates to proteosome vaccines in which meningococcal outer membrane protein proteosome preparations (prepared from any strain of *N. meningitidis* or *N. gonorrhea* or other neisserial species) are non-covalently complexed to native or detoxified shigella or neisserial lipopolysaccharides or lipooligosaccharides to form vaccines designed to protect against diseases caused by gram negative organisms that contain any of the component parts of the complex including meningococci or shigellae. More specifically, the invention relates to proteosome vaccines that contain LPS that induce antibody responses that recognize type-specific somatic polysaccharide O-antigens of shigella lipopolysaccharides and thereby confer homologous protection against shigellosis. Still more specifically, the lipopolysaccharides that, when complexed to proteosomes induce such anti-shigella protective immune responses are prepared and purified from either *Shigella sonnei* or *Plesiomonas shigelloides* for immunity against *Shigella sonnei* disease, from *Shigella flexneri* 2a for immunity to *Shigella flexneri* 2a disease, and so forth, using LPS derived from homologous or antigenically cross-reacting organisms to confer homologous immunity against shigellosis caused by *S. flexneri* 2a (or 3a etc.), *S. boydii, S. sonnei* etc. Still more specifically, the instant invention describes the successful administration of proteosome-shigella vaccines that are multivalent in that two independently made proteosome vaccines using shigella LPSs derived from *S. flexneri* 2a (for *S. flexneri* 2a disease) and from *P. shigelloides* or *S. sonnei* (for *S. sonnei* disease) are administered together thereby inducing antibodies that recognize the two organisms and thereby conferring protection against the two types of diseases. Most specifically, the instant invention relates to a proteosome-shigella LPS vaccine in which proteosomes from group B type 2b meningococci are complexed to *P. shigelloides* LPS using hollow fiber diafiltration technology to produce a vaccine administered by mucosal respiratory and/or gastro-intestinal routes to induce antibodies that recognize the somatic O-antigen LPS of *S. sonnei* and thereby protect against shigellosis caused by this organism. Other conventional ultrafiltration/diafiltration are envisioned, e.g. platform membrane and membrane cartridge.

The present invention provides methodology to produce non-covalently complexed vaccines in a manner that 1) Decreases the time required, 2) Decreases the opportunity for contamination, 3) Increases the temperature to ambient temperature that such vaccines can be produced, 4) Allows for efficient scale-up of the production process so as to require minimum use of reagents, 5) Allows for reliable and efficient sampling of dialysate so as to be able to repeatedly measure rate of removal of the detergent so as to optimize efficiency of the operation. This leads directly to an increase in the complexing efficiency of vaccine so as to produce vaccine with measurably greater immunogenicity at lower doses. In this manner, the overall quality of the product is significantly enhanced. 6) In addition, a method is described to measure the presence of the detergent used in the preferred embodiment, Empigen BB. Other dialyzable detergents can be used in place of Empigen BB. Furthermore, using the method of the instant invention, it has been demonstrated that the vaccine can be lyophilized and re-hydrated in such a manner as to retain optimal vaccine potency as measured by vaccine immunogenicity.

The method of the instant invention entails the use of a hollow fiber ultrafiltration/diafiltration cartridge to effect complexing by removal of the detergent. By varying the size of the housing of the cartridge, the time of dialysis for production of a lot of vaccine can be reduced from >7–10 days to less than 72 hours and usually less than 48 or 24 hours. Since this short time is used, the reaction temperature can be increased from 4° to normal room temperature without compromising the process or the integrity of the products. While the process was performed at about 20° C., temperatures between 0° and 40° C. are contemplated. Since the system is closed, there is a highly reduced potential for contamination. In addition, by increasing the size of the housing, an exceedingly large amount of material can be processed in a relatively short period of time thereby allowing for efficient and reproducible scale-up of the procedure for commercial development. Furthermore, the permeate can be repeatedly sampled to measure the removal of the detergent as can be accomplished using the test of the instant invention to measure the presence of the detergent empigen BB, the detergent used in the preferred embodiment. The uniqueness of this methodology needed experimental verification since it was not obvious that the complexing and the structure of the vaccine into immunogenic materials that was accomplished by slowly dialyzing over 7–10 days using a stationary dialysis bag could be equalled or improved upon using the hollow fiber technology in which the moieties to be complexed are moving through tubes at exceedingly high flow rates compared to that of the stationary dialysis tube.

Since the nominal molecular weight cutoff of the membrane used can be selected to be from 1,000, 3,000, 5,000, 10,000, 30,000, 50,000 or greater, depending on the size of the components to be non-covalently complexed, this system is readily adaptable to the complexing of native or detoxified lipopolysaccharides, lipids, peptides, lipopeptides, liposaccharides, polysaccharides, gangliosides or transmembrane, envelope or native or toxoided proteins to each other or to meningococcal outer membrane protein preparations of proteosomes.

The resultant product can be used as a vaccine administered either parenterally or mucosally i.e. via the respiratory or gastro-intestinal tract e.g. intranasally, orally, by oropharyngeal inhalant, topically or rectally. In the example given, it is shown that proteosomes are non-covalently complexed to *P. shigelloides* LPS to form a vaccine that induces the anti-*S. sonnei* LPS responses necessary for protection against *S. sonnei* shigellosis.

The methodology has three stages: a preliminary operation; complexing the proteosome with an amphiphilic determinant e.g. *P. Shigelloides* LPS; followed by a sterile filtration.

To optimally deliver multivalent vaccines, the present invention shows that the best method is to make the specific vaccines individually and then immunize with the two individually made vaccines, each at the optimal concentration, on the same day. Other possibilities such as making hybrid vaccines during the formation of the non-covalent complexes have also been accomplished or are envisioned.

BRIEF DESCRIPTION OF THE FIGURES

FIG. 7: Intranasal or oral immunization of humans with one or two doses proteosome-*p. shigelloides* LPS vaccines for *Shigella sonnei* using different vaccine amounts: Induction of anti-shigella LPS IgA, IgG and IgM peripheral blood ASC responses, and serum, salivary and urinary antibody responses.

5. DETAILED DESCRIPTION OF THE INVENTION

Example 1

This example is detailed for production of proteosome-*P. shigelloides* vaccine containing approximately 2–3 grams of protein. The procedure is equally applicable for scale-up using 10–1000 fold more material with appropriate scale-up of housing size of the membrane cartridge and appropriate increases in the volumes. Using the appropriate size membranes with appropriate size molecular weight cutoffs to retain the antigens to be complexed, this procedure is equally applicable for complexing of proteosomes to other native or detoxified lipopolysaccharides, lipids, peptides, lipopeptides, liposaccharides, polysaccharides, gangliosides or transmembrane, envelope or native or toxoided proteins to each other or to meningococcal outer membrane protein preparations of proteosomes. Empigen BB is the detergent used as an example in this procedure; the procedure applies equally to any dialyzable detergent that solubilizes the components. This procedure uses A/G technology cartridges but is equally applicable to any brand cartridge type ultrafiltration/diafiltration system.

5.0.0.1 Preliminary Operation 5.0.0.1. Sterile filter a stock solution of 30% Empigen BB, which is the detergent used in this process.

5.0.0.2. Prepare 2×TEEN/2% Empigen (0.1M Tris, 0.02 M disodium EDTA, 0.3 M sodium chloride, WFI and 2% Empigen, pH 8.0)

5.0.0.3. Prepare 150 L of a TNS (Tris Normal Saline) solution containing 0.05M Tris, 0.15M sodium chloride pH 8.0 for the purpose of dialyzing out the detergent.

5.0.0.4. Prepare 10 liters of Sodium Hydroxide for UF cartridge cleaning.

5.0.0.5. Thaw the required amount of *Shigella flexneri* 2a Lipopolysaccharide (LPS).

5.0.1. Complexing Proteosomes with *S. flexneri* 2a LPS 5.0.1.6. Add an equal volume of 2×TEEN buffer to the volume of LPS and mix well.

5.0.1.7. Thaw and measure an amount of bulk proteosomes, in mg's, equal to the amount of LPS thawed in step 5.

5.0.1.8. To the proteosomes, add 30 ml of sterile filtered empigen per liter. Mix well and combine with the LPS from step 5.

5.0.1.9. Mix both components well. Usually 15 minutes on a stir plate and stir bar combination is adequate.

5.0.1.10. To dialyze the detergent out so that proteosome complexes could form, set up an ultrafiltration system (based on tangential flow technology} using a hollow fiber cartridge with a nominal molecular weight cutoff (NMWC) pore size of 10,000 manufactured by A/G Technology, Inc. connected to sterilized silicone tubing and a peristaltic pump. Sanitary pressure gauges are placed on the inlet and outlet side of the cartridge to monitor pressure throughout the run. A back pressure valve is placed on the outlet side of the cartridge to as to adjust back pressure.

5.0.1.11. The ultrafiltration system is cleaned and sanitized with WFI and 0.5N NaOH at a temperature of 50° C. for a time greater than 60 minutes. This system is flushed with WFI and equilibrated with TNS buffer prior to use.

5.0.1.12. A sterile reservoir vessel is placed in line so that the inlet liquid is pulled from the vessel and the return retentate returned to the same reservoir. As liquid passes through the cartridge membrane (permeate or filtrate) it is replenished by TNS buffer either by direct addition or by a continuous feed system. Set up a continuous feed system by connecting silicone tubing to a vessel containing TNS buffer to the sample reservoir that is then air tight. As the liquid is removed by filtration from the sample reservoir a vacuum is created causing "TNS" buffer to be pulled from the its vessel into the sample reservoir. If the system remains air tight the sample level it the reservoir remains constant.

5.0.1.13. Start the recirculation pump to begin diafiltration. Adjust the pump speed and the back pressure valve to obtain a back pressure of 15±4 psi.

5.0.1.14. Verify progressive removal of Empigen BB by testing permeate samples taken every 10–15 liters using the Empigen Precipitin Test. This test consists of making serial dilutions of the permeate and of a standard solution containing a known quantity of empigen BB, adding HCl to acidify the solutions and then adding serial dilutions of SDS (sodium dodecyl sulfate) to form a checkerboard-type assay. Maximum precipitate will form when equivalent amounts of empigen and SDS are present. In this manner, the amount of empigen present can be quantitated by noting the dilution of the SDS, the permeates and of the standards at which the maximum precipitate is formed. As the diafiltration progresses, the amount of empigen becomes less and the tube containing less SDS will be the tube with the maximum precipitate. The presence of precipitate is quantitated by measuring the OD at 600 nm using a spectrophotometer.

5.0.1.15. For the amount of components used in this example, continue diafiltration until at least 120 liters of permeate has been processed and there is a lack of significant precipitate in the Empigen Precipitin Test (Maximum OD 600 nm is less than 0.05).

5.0.1.16. After dialysis is complete concentrate the product to a final volume to get an $OD_{280}$ value close to 6.0. Drain the system and wash with 300–400 ml of "TNS" buffer. Drain the system again and combine both pools. Clean the cartridge by recirculating large amounts of WFI followed by 0.5N NaOH at 50° C. for >60 minutes. Rinse out the NaOH with WFI and store the system in 0.01N NaOH.

5.0.2. Sterile Filtration 5.0.2.17. The complexes may, if desired, be sterile filtered. Proteosome concentration can be adjusted before or after $0.22\mu$ filtering. Sterile filtration is normally performed with filter units from Millipore Corp. These units are called Millipaks and they come in various sizes. The filtered bulk is stored at 4° C. until the fill operation and is tested for sterility.

5.0.3.0 Specific Purpose

Combine bulk GMP preparations of meningococcal outer membrane protein proteosomes and *S. flexneri* 2a lipopolysaccharide into non-covalent complexes by removal of detergent.

5.0.3.1 Applications

This GMP procedure results in the production of a bulk preparation formation of non-covalent complexes of proteosomes with *S. flexneri* 2a lipopolysaccharide for use as a vaccine against *S. flexneri* 2a infection.

Example 2

Noncovalent complexing of bulk *Neisseria meningitidis* strain 9162 purified outer membrane proteins (proteosomes) and alkaline detoxified *N. meningitidis* L8 lipooligosaccharide purified from strain 8532.

5.1.0 Bulk 9162 outer membrane protein (proteosomes), lot 0136 and bulk detoxified meningococcal L8 Lipooligosaccharide (LOS) lot 0203 were taken from storage and thawed at room temperature. A volume (182 ml) of the bulk LOS containing 500 mg LOS in sterile distilled water was combined with a volume (306 ml) of bulk proteosomes containing 400 mg of protein in buffer containing 0.05 M Tris-HCl, 0.15 M NaCl, 0.01 M EDTA, and 0.1% Empigen BB.

5.1.2 Empigen BB (30% solution) was sterile filtered through a 0.22 μm pore size filter and $1/60^{th}$ volume added to the combined proteosomes, LOS solution and stirred at room temperature for 1 hour.

5.1.3 The detergent buffer solution was removed from the proteosomes, LOS solution and replaced with sterile distilled water by ultrafiltration using an A/G Technology ultrafiltration cartridge UFP-3-C-6 with a 3000 molecular weight cut off pore size.

5.1.4 The procedure for set up, sanitization, washing, washing, and cleaning of the apparatus was the same as described in example 1. Inlet pressure was 15±4 PSI and the permeate flow rate was 175 ml per minute.

5.1.5 The permeate was tested after each 3 to 4 liters for the presence of Empigen BB detergent by the precipitation method described in example 1. The ultrafiltration was continued until no precipitate was obtained in the test plus an additional 5 liters. A total of 37 liters of permeate was collected.

5.1.6 The retentate was clear and was sterile filtered through a 0.22 μm pore size filter assayed for protein and LOS and stored as a bulk product at 4° C.

5.1.7 The bulk product was diluted to a concentration of 0.2 mg of protein per ml and the concentration of NaCl adjusted to 0.15 M. Thimerasol at 0.01% was added as a preservative, and the resulting bulk was dispensed under sterile conditions into final container vials, labelled and stored at −70° C.

5.1.8 This product was tested in mice for immunogenicity when given as a saline solution and adsorbed to aluminum hydroxide gel as adjuvant. The results are given in the Table 1 below and show that the vaccine complexes were immunogenic when given i.p. in mice.

TABLE 1

Bactericidal antibody response of mice to meningococcal outer membrane protein-detoxified lipooligosaccharide vaccine, geometric mean reciprocal titers against meningococcal strain 9162

| Vaccine | Dose | Adjuvant | Day 0 | Day 28 | Day 42 |
|---|---|---|---|---|---|
| proteosomes- | 1 μg | None | <8 | <8 | 16 |
| dLOS | 3 μg | None | <8 | <8 | 128 |
| Lot 0271 | 10 μg | None | <8 | <8 | 512 |
| protesomes- | 1 μg | $Al(OH)_3$ | <8 | <8 | 512 |
| dLOS | 3 μg | $Al(OH)_3$ | <8 | <8 | 512 |
| Lot 0271 | 10 μg | $Al(OH)_3$ | <8 | 64 | 2048 |

Note: Vaccine was given intraperitoneally at 0 and 28 days to groups of ten outbred CD-1 mice.

5.1.9 The complexing of the proteosomes and LOS was verified by column chromatography of the proteosomes and LOS components before and after complexing (FIG. 9). Chromatographic analysis of bulk meningococcal L8 LOS and the final proteosomes/LOS complexes on Sephacryl S300 low pressure column. The column was run in 0.05 M Tris-HCl, 0.01 M EDTA, 0.15 M NaCl buffer. The assay for protein was by absorbance at 280 nm, and the assay for LOS was by inhibition of an ELISA (enzyme linked immunosorbant assay) in which an L8 monoclonal antibody binding to purified L8 LOS adsorbed to the plastic plate was inhibited by serial dilutions of the fractions off the Sephacryl column. Before complexing, the LOS came off the column in a broad peak centered at fraction 39. After complexing, the LOS co-eluted with the proteosomes in a peak approximately centered at fraction 33.

5.1.10 Specific Purpose

Combine bulk GMP preparations of meningococcal outer membrane protein proteosomes and detoxified meningococcal lipopolysaccharide into non-covalent complexes by removal of detergent.

5.1.11 Applications

This GMP procedure results in the production of a bulk preparation formation of non-covalent complexes of proteosomes with detoxified meningococcal lipopolysaccharide for use as a vaccine against *N. meningitides* (meningococcal) infection.

Example 3

This example is also directed to the production of proteosome-*P. shigelloides* vaccine. The procedure is equally applicable for scale-up using 10–1000 fold more material with appropriate scale-up of housing size of the membrane cartridge and appropriate increases in the volumes.

5.8.1 Preparation of 25 mL Sterile-Filtered Empigen BB (30% Solution)

5.8.1.1 Use a 100 ml Nalgene disposable filter unit with 0.2μ pore size membrane filter to sterile filter about 25 ml of Empigen BB (30% solution).

5.8.2 Prepare 4 L of TEEN 2× with 2% Empigen BB (consisting of 0.1 M Tris, 0.02 M disodium EDTA, 0.3 M sodium chloride, WFI and 2% solution of empigen BB).

5.8.3 Prepare a 10 L solution of "TNS" fifteen times to total 150 liters: TNS consists of 0.15 M sodium chloride, 0.05 M Tris Buffer pH 8.0±0.2

5.8.4 Prepare 10 liters of 0.5 N Sodium Hydroxide 5.8.6 If necessary, thaw bulk *P. shigelloides* lipopolysaccharide (LPS) to prepare for complexing with proteosomes and record the lot number, and concentration of the LPS, the required amount of LPS in mg and the calculated volume of LPS to remove. ps 5.9.0 Complexing Proteosomes with *P. shigelloides* LPS 5.9.1 Preparation of LPS for Complexing 5.9.1.2 Pool the aliquots of bulk LPS into a clean, sterile, calibrated 5 L bottle. Measure the total volume and determine the total amount of LPS.

5.9.1.3 Add a volume of 2×TEEN buffer equal to the volume of LPS used in step 5.9.1.2, measure combined total volume, and then add a stir bar and mix with stir bar and stir plate combination for 15±2 minutes.

5.9.2 Preparation of Proteosomes for Complexing 5.9.2.1 Record the total time, if any, proteosomes was allowed to thaw.

5.9.2.2 Pool the aliquots of bulk proteosomes into a clean, sterile, 1 L graduated cylinder. Measure the total volume and determine the total amount of proteosomes.

5.9.2.3 From the cylinder in step 5.9.2.2, transfer to another clean, sterile, 1 L graduated cylinder, a volume of proteosomes containing the amount in mg equal to the mg amount of LPS used in step 5.9.1.2.

5.9.2.4 To the cylinder containing the proteosomes, add 0.22μ filtered 30% empigen BB using 30 ml empigen per L proteosomes. Mix with a stir bar for 15±2 minutes.

5.9.3 Combine Protesomes with the *P. Shigelloides* LPS 5.9.3.1 Under gentle stirring with a stir bar, add the proteosomes from step 5.9.3.2 to the graduated 5 L bottle with the LPS and stir for 15±2 minutes.

5.9.3.3 Remove four 1 ml samples and store at −75° C. for later measurement of the concentration of protein by the Lowry method and LPS by KDO assay.

5.9.4 Removal of Detergent by Ultrafiltration/Diafiltration 5.9.4.1 Ultrafiltration System Details System: A/G Technology, Inc. hollow fiber cartridge, 10,000 NMWC pore size, housing size 6, ultrafiltration cartridge Note:It is necessary to condition new cartridges to flush out glycerol. This can be done by flushing 6 liters of WFI through the 6 sq/ft cartridges or less with no back pressure. The permeate solution should not be recycled to the feed reservoir. Note:All ultrafiltration steps will be follow by cleaning, sanitization, and storage steps. New cartridges have to be cleaned and sanitized prior to use.

5.9.4.2 Set-up and sanitize the A/G ultrafiltration system. Clean and sanitize the system by recirculating for a minimum of 60 minutes with 2–3 liters of 0.5 N Sodium Hydroxide at an initial temperature of 50±5° C. Flush the system with 4–5 liters of WFI followed by recirculating 2–3 liters of "TNS" (0.05 M Tris/normal saline buffer pH 8.0±0.2, for at least 20±5 minutes.

5.9.4.3 Measure the hold up volume in the UF system (including tubing) by transferring inlet and outlet lines filled with liquid out of the reservoir and into a 1 liter graduated cylinder, then pump until the UF system is empty.

5.9.4.4 Place a 2 liter side-armed vessel in a pan and pack the vessel with wet ice for the duration of the diafiltration procedure.

5.9.4.5 Transfer 1.7–1.9 L of the bulk proteosome-LPS mixture from step 5.9.3.3 into the 2 L side-armed vessel. Place a two-holed stopper fitted with two 10 ml pipettes on the vessel and connect the inlet and outlet tubing from the diafiltration system to the vessel pipettes.

5.9.4.6 Turn on the recirculation pump and adjust the pump setting to 4–6. Adjust the back pressure clamp to obtain an inlet pressure of 15±4 psi. Concentrate to a total volume of 1.0±0.1 L including the hold-up volume 5.9.4.7 Transfer 1±0.1 L of mixture from step 5.9.3.3 to the 2 L side-armed vessel and repeat step 5.9.4.6.

5.9.4.8 Continue transferring as in step 5.9.4.7 and concentrating as in step 5.9.4.9 until all the proteosome-LPS mixture from step 5.9.3.3 has been transferred to the 2 L side-armed vessel and the retentate volume is 1.4±0.2 L which includes the hold-up volume 5.9.4.10 Set up the ultrafiltration apparatus for continuous feed of TNS (0.05 M Tris, normal saline) into the 2 liter side-armed vessel as liquid is removed through the membrane. Set up a reservoir using a 10 liter bottle containing TNS and fitted with a tube extending to the bottom of the bottle. Connect the inlet and outlet lines from the ultrafiltration system. Turn on the recirculation pump and adjust the pump setting to 4–6. Adjust the back pressure clamp to obtain an inlet pressure of 15±4 psi.

5.9.4.11 Measure the permeate flow rate on the UF unit and record the inlet pressure when the measurement is taken.

5.9.4.12 Collect a 15 to 20 ml sample of the permeate every 12±0.5 liters processed, apply an in-house label ("Permeate No. P1, P2, P3 etc.") and record the time, volume processed and maximum $O.D._{600}$ of the sample. Verify progressive removal of empigen by testing the samples for the presence of Empigen BB using the Empigen Precipitin Test. This test consists of making serial dilutions of the permeate, and, separately, of a solution containing a known quantity of empigen BB, adding HCl to acidify the solutions and then adding serial dilutions of SDS (sodium dodecyl sulfate) to form a checkerboard-type assay. Maximum precipitate will form when equivalent amounts of empigen and SDS are present. In this manner, the amount of empigen present can be quantitated by noting the dilutions of the permeates and the SDS in which the precipitate is formed and comparing those dilutions to those of the standards. As the diafiltration progresses, the amount of empigen becomes less and the tube containing less SDS will be the tube with the maximum precipitate. The presence of precipitate is quantitated by measuring the OD at 600 nm using a spectrophotometer.

For the amounts of components used in this example, continue diafiltration until at least 120 liters of permeate has been processed and there is a lack of significant precipitate in the Empigen precipitin test (Maximum OD 600 nm less than 0.05).

5.9.4.13 Concentrate the product to a final retentate volume of 500±50 ml including the hold-up volume (step 9.4.3). Remove a 0.5 ml sample, dilute the sample 1:10, and measure the $O.D._{280}$.

5.9.4.14 The desired minimum O.D. of the concentrated retentate is 5.7. If the O.D. is less than 5.7, continue concentrating to 400±50 ml including the hold-up volume (step 5.9.4.3) and repeat the $O.D._{280}$.

5.9.4.15 With the retentate lines out of the retentate solution and the filtrate outlet lines closed, slowly pump in the reverse direction until the cartridge and lines are empty. Transfer the feed line and retentate lines from the retentate bottle to a new clean vessel with 350±50 ml TNS. Reverse the pump and slowly recirculate the TNS for 2–3 minutes.

5.9.4.16 After recirculating the TNS, stop the pump, drain the system, collect the retentate wash solution into a clean, sterile, 1 L graduated cylinder and measure the volume and the O.D.$_{280}$.

5.9.4.17 Combine the original retentate solution (step 5.9.4.12 or 5.9.4.13) with the wash retentate solution (step 5.9.4.15) and measure the final volume of retentate. Store the retentate bulk at 4° C.±2° C. until aseptic filtration.

5.9.4.18 Clean the filtration unit using WFI, followed by 0.5 N sodium hydroxide at an initial 50±5° C. for a minimum of 60 minutes. Rinse the cleaning agent out with of WFI then flush with 3–4 liters of 0.1 N NaOH as the storage agent.

5.9.5 Sterile Filtration

The complexes may, if desired, be sterile filtered. Obtain the bulk complexed proteosomes and LPS and inspect for the presence of any precipitate or cloudiness. If the bulk complexed product is clear, aseptically filter it using a Millipak 40, 0.22μ filtration unit into a sterile, depyrogenated vessel. This step is to be done in a Sterile Cabinet.

5.9.6 Specific Purpose

Combine bulk GMP preparations of meningococcal outer membrane protein proteosomes and *P. shigelloides* lipopolysaccharide (for *S. sonnei*) into non-covalent complexes by removal of detergent.

5.9.7 Applications

This GMP procedure results in the production of a bulk preparation formation of non-covalent complexes of proteosomes with *P. shigelloides* 2a lipopolysaccharide for use as a vaccine against *Shigella sonnei* infection.

5.10 Immunogenicity Studies 5.10.1 Immunogenicity of Proteosome-*P. ShigelloideS* LPS Vaccine Using Hollow Fiber Ultrafiltration/Diailtration FIGS. 1 and 2 demonstrate that three different proteosome-shigella LPS vaccine preparations made using the hollow fiber (HF) diafiltration technique (HF-1, HF-2 and GMP/HF-3) to remove detergent and facilitate complexing are more effective at the lowest, most stringent dose tested, than preparations made using simple dialysis tubing (DT). In other words, stronger IgG (FIG. 1) and IgA (FIG. 2) immune responses were elicited by vaccines produced using the instant invention than by the older, less efficient technology. Since stronger immune responses result in better levels of protection, these data clearly show that the instant invention results in vaccines that are not only more efficient to make but also more powerful. Furthermore, the stronger responses are elicited by the vaccine when administered at the lowest dose (0.1 ug per dose) thereby indicating that less vaccine would be needed using the instant invention than would be required using the older technology. Since in the formulation of multivalent vaccines requires many different antigens, in order to minimize the total amount of vaccine administered, it is highly advantageous to be able to use vaccine components that are effective at lower doses. Thus, the technology of the instant invention to produce vaccines using the hollow fiber technology directly impacts and facilitates the ability to formulate multivalent vaccines having a wide range of specificities. Since it is advantageous for commercial development of vaccines to be able to lyophilize vaccines, we were gratified to discover that lyophilization of the HF vaccine complexes from a water solution, surprisingly resulted in vaccine that consistently elicited responses that were among the highest at all doses tested. Thus, higher immunogenicity for anti-LPS IgG FIG. 1) and IgA (FIG. 2) was found when 0.1 ug of vaccine made by the HF technique (with or without lyophilization) was administered. These data are significant since the scale-up and GMP procedure of the instant invention used the HF technology as indicated in FIGS. 1 and 2 by the cross-hatched bar representing GMP/HF-3.

5.10.2 Immunogenicity Studies Using Multivalent Vaccine

As shown in FIG. 3, Administration of the proteosome-*P. shigelloides* LPS (for *S. sonnei* shigellosis) and the proteosome-*S. flexneri 2a* vaccines on the same day or weeks apart results in good immunogenicity to both LPS components: *S. sonnei* LPS and *S. flexneri 2a* LPS. Scheduled 1 consisted of five mice intranasally immunized on days 0 and 21 with the proteosome- *S. sonnei* LPS vaccine (10 micrograms each of proteosomes and LPS). Mice were bled four weeks after the last immunization. Scheduled 2 consisted of five mice intranasally immunized on days 0 and 21 with the proteosomes-*S. flexneri 2a* LPS vaccine (10 micrograms each of proteosomes and LPS). Mice were bled four weeks after the last immunization. Schedule 3 consisted of five mice intranasally immunized on days 0 and 21 with the proteosomes-*S. flexneri 2a* LPS vaccine (10 micrograms each of proteosomes and LPS). Mice were bled four weeks after the last immunization. Schedule 4 consisted of four mice intranasally immunized on days 0 and 21 with the proteosome- *S. sonnei* LPS vaccine (10 micrograms each of proteosomes and LPS) and then on days 49 and 70 with the *S. flexneri 2a* LPS vaccine (10 micrograms each of proteosomes and LPS). Mice were bled four weeks after the last *S. flexneri 2a* immunization.

5. 11 Electron Micrograph of Proteosome-Shigella Vaccine

The association of shigella LPS with proteosomes is clearly and dramatically depicted in the electron micrograph shown in FIG. 4. In this Figure, the proteosome vesicles are studded with radio-opaque black dots. These dots are god beads linked to secondary antibodies that recognize specific anti-shigella LPS antibodies. Thus, the presence of gold dots indicates the presence of shigella LPS. Since, as can be seen, the gold dots surround and dot the proteosome vesicles, the image of proteosome vaccines with LPS non-covalently linked to the proteosomes is thereby confirmed and visualized. Surprisingly, the consistent vesicular nature of the vaccines made with the HF technology of the instant invention was not found when the DT preparations using the older technology were examined by electron microscopy (unpublished results).

5.12 Proteosome-*P. Shigelloides* LPS Vaccine Protects Against Lethal *Shigella Sonnei* Pneumonia in an Animal Model of Shigellosis As can be seen in FIG. 5, the proteosome-*P. shigelloides* LPS vaccine consistently confers highly significant protection against lethal infection with *P. shigelloides* as measured in an animal model of shigellosis in which the animals are challenged with live organisms to induce lethal pneumonia. These data also demonstrate that not only are the correct and protective antibodies produced by the proteosome-*P. shigelloides* LPS vaccine, but also that this intranasal sub-unit vaccine can protect against lethal pneumonia. Groups of outbred mice (14 to 15 per group) were immunized intranasally on weeks zero and three with the proteosome-*P. shigelloides* LPS vaccine (10 micrograms each of proteosomes and LPS per 20 mircoliters). Control groups were given saline on the same schedule. All mice were challenged intranasally with five to ten million colony forming units of *S. sonnei* on week seven. The mice were observed daily for two weeks after challenge, and mortality resulting from the ensuing pulmonary disease was recorded. As we have shown previously, 86 to 100% of the control mice die within four days after challenge. In both experiments, 93% of mice immunized with the vaccine survived challenge (P<0.001, Fisher's Exact Test).

5.13 Intranasal or Oral Immunization with Proteosome-*Shigella flexneri* 2a LPS Vaccines Induce Anti-Shigella LPS IgG and IgA in Serum and IgA in Intestinal and Lung Lavage Fluids That Can Last 30–60 Days Post-immunization.

As shown in FIG. 6, two immunizations with proteosome-*shigella flexneri* 2a LPS vaccines induce antibodies in sera and in lung and intestinal secretions that can last 30 to 60 days post immunization. These data show that proteosome vaccines can stimulate the common mucosal immune system to secrete specific antibodies even at locations far away from the immunizing site. Specifically, intranasal immunization can induce antibodies in intestinal secretions and vice versa. This ability expands the potential utility of proteosome vaccines to protect against pathogens that invade the host through the mucosal portals of entry throughout the body.

5.14 FIG. 7 shows the induction of anti-shigella LPS IgA, IgG and IgM peripheral blood ASC responses, and serum, salivary and urinary IgA and IgG antibody responses after intranasal or oral immunization of human volunteers with one or two doses proteosome-*P. shigelloides* LPS vaccines for *Shigella sonnei* using different vaccine amounts. As shown, intraasal immunization elicited responses in a dose dependant fashion with the highest dose inducing responses in all six volunteers.

IgA, IgG and IgM serum responses were elicited in each of the intranasal groups. In addition, strong antibody secreting cell ASC responses were induced indicating that mucosal immunization stimulated trafficking of antibody secreting cells—most notably, IgA-secreting cells. Most importantly, IgA responses were also found in salivary and, especially, urinary samples indicating that secretory IgA was produced at mucosal surfaces (since IgA does not pass through the kidney, the urinary IgA reflects local secretion of antibody and suggests that such intranasal vaccines also produce local intestinal IgA and that intranasal vaccines could be used to protect against urinary tract infections caused by gram negative organisms.) It is noteworthy that the majority of these ASC and antibody responses were found after only one immunization suggesting that booster immunization may not be necessary. IgA and IgG ASCs and urinary IgA were also found after oral immunization. The most effective use of oral administration may be as a booster immunization after nasal priming, if necessary.

Figure 1:
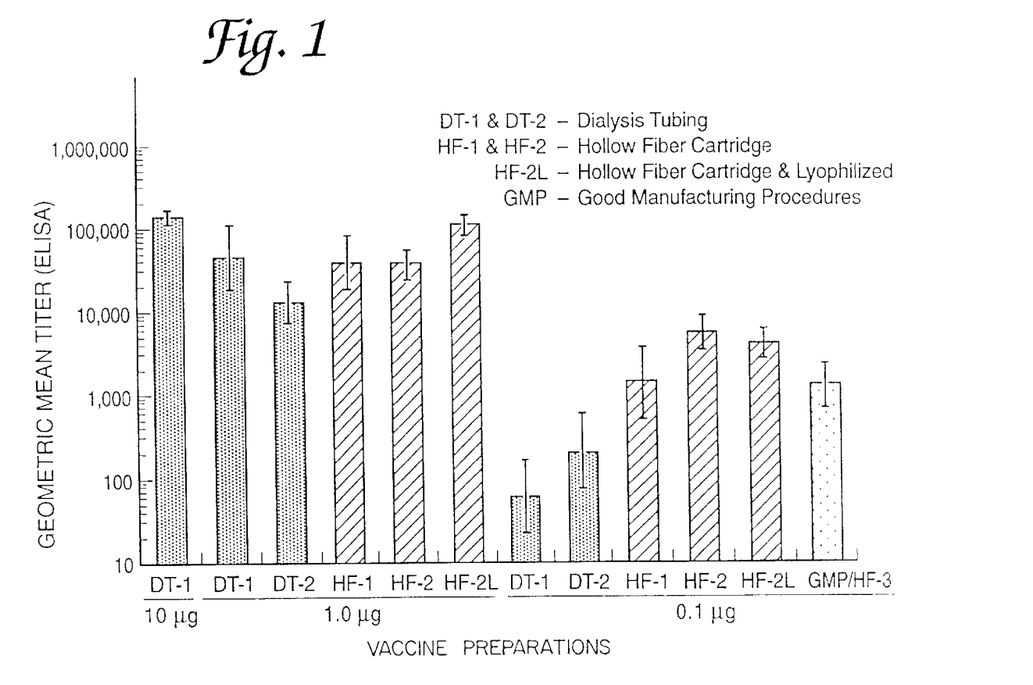
FIG. 1: Intranasal immunization with proteosome-*P. shigelloides* LPS Vaccine: serum IgG responses elicited by several preparations at decreased doses.
Figure 2:
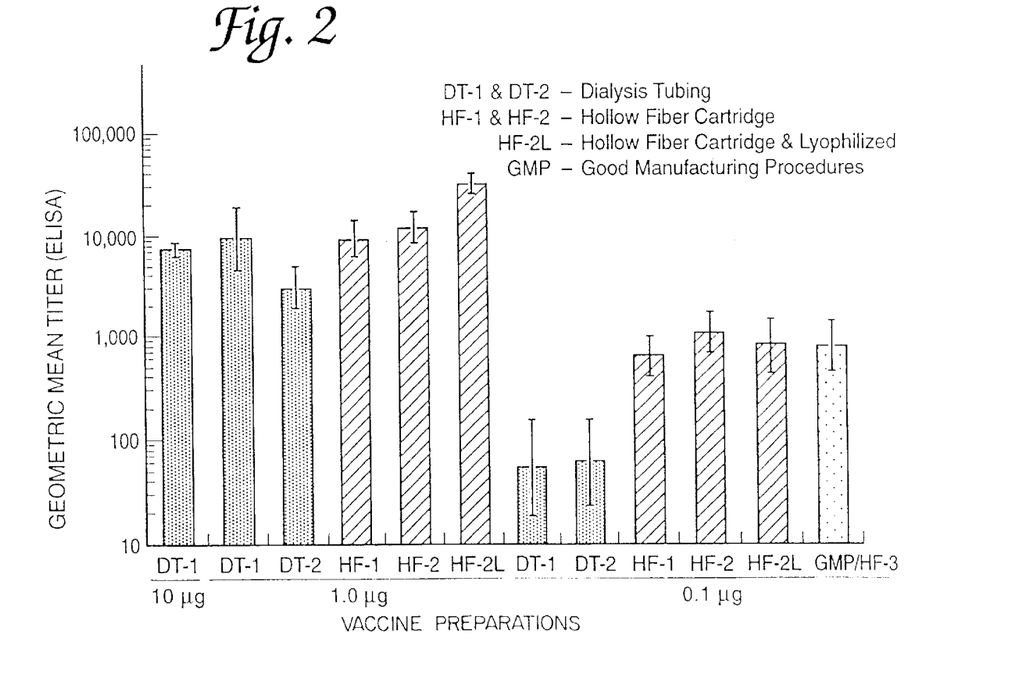
FIG. 2: Intranasal immunization with Proteosome-*P. shigelloides* LPS vaccine: serum IgA responses elicited by several preparations at decreased doses.
Figure 3:
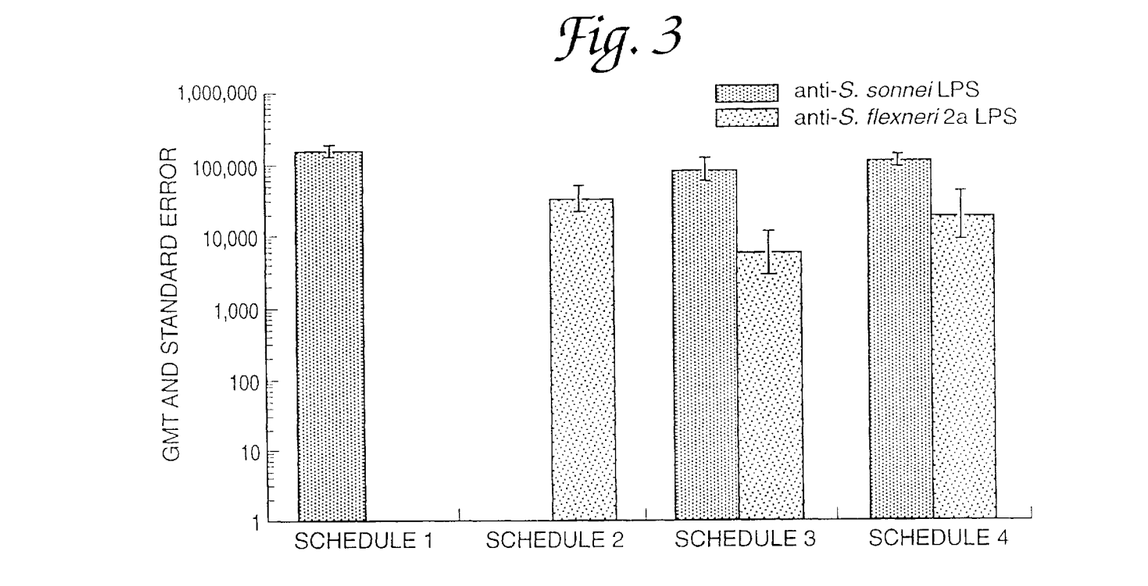
FIG. 3: Administration of the proteosome-*P. shigelloides* LPS (for *S. sonnei* shigellosis) and the proteosome-*S. flexneri* 2a vaccines together on the same day or weeks apart results in good immunogenicity to both the *S. sonnei* and *S. flexneri* 2a LPS components.
Figure 4:
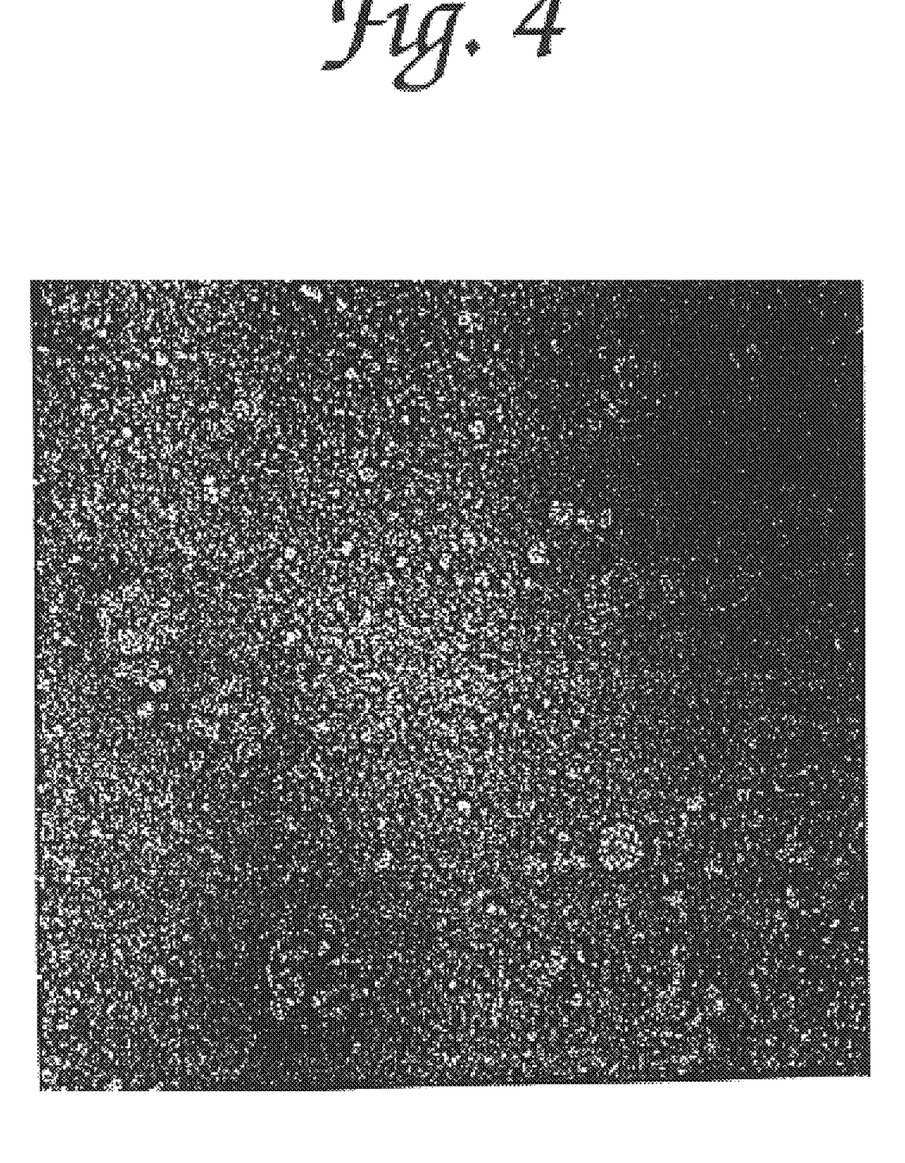
FIG. 4: Immunogold labelled electron micrograph of proteosome-shigella LPS vaccine showing association of shigella LPS with proteosome vesicles.
Figure 5:
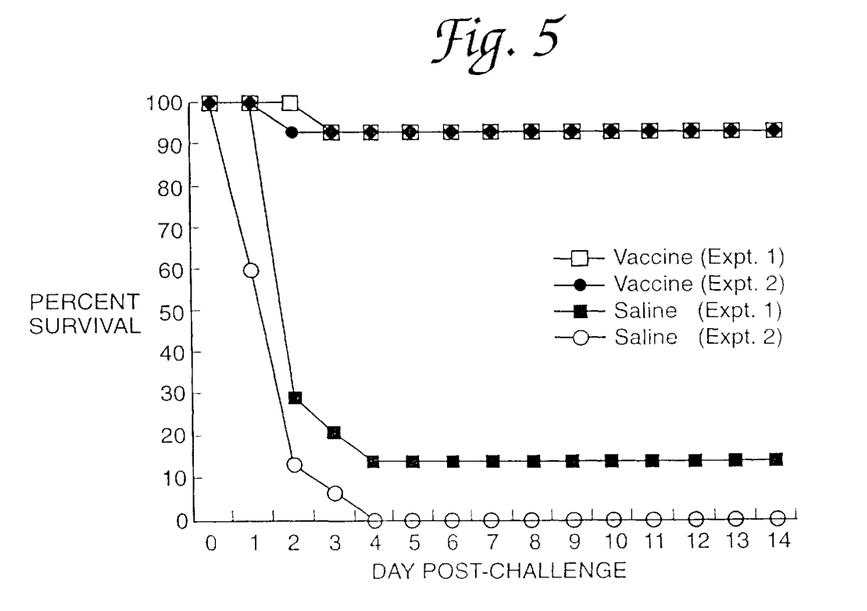
FIG. 5: Proteosome-*P. Shigelloides* LPS vaccine protects against lethal *Shigella sonnei* pneumonia in an animal model of Shigellosis.
Figure 6A:
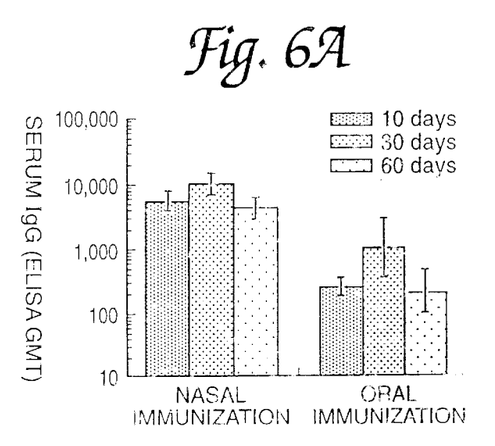
FIGS. 6A–D: Intranasal or oral immunization with proteosome-*Shigella flexneri* 2a LPS vaccines induce anti-shigella LPS IgG and IgA in serum and IgA in intestinal and lung lavage fluids that can last 30–60 days post-immunization.
Figure 6B:
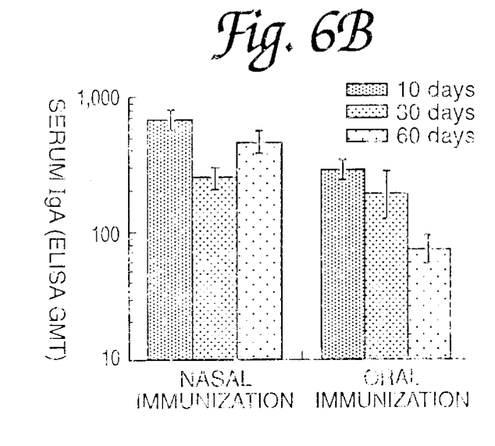
Figure 6C:
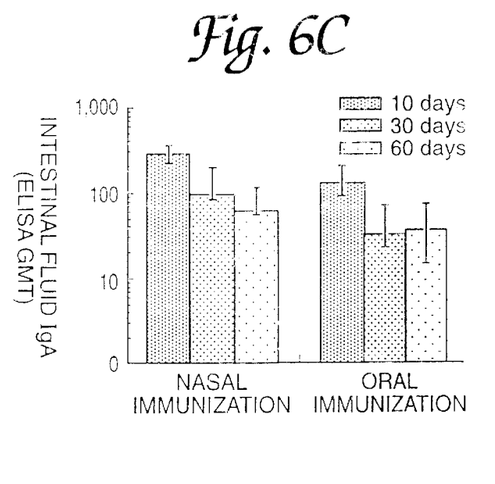
Figure 6D:
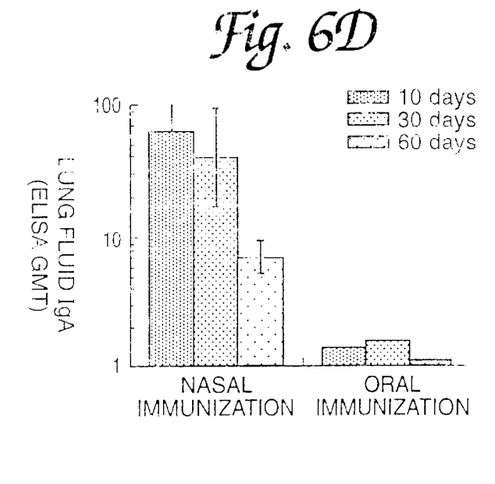
Figure 8:
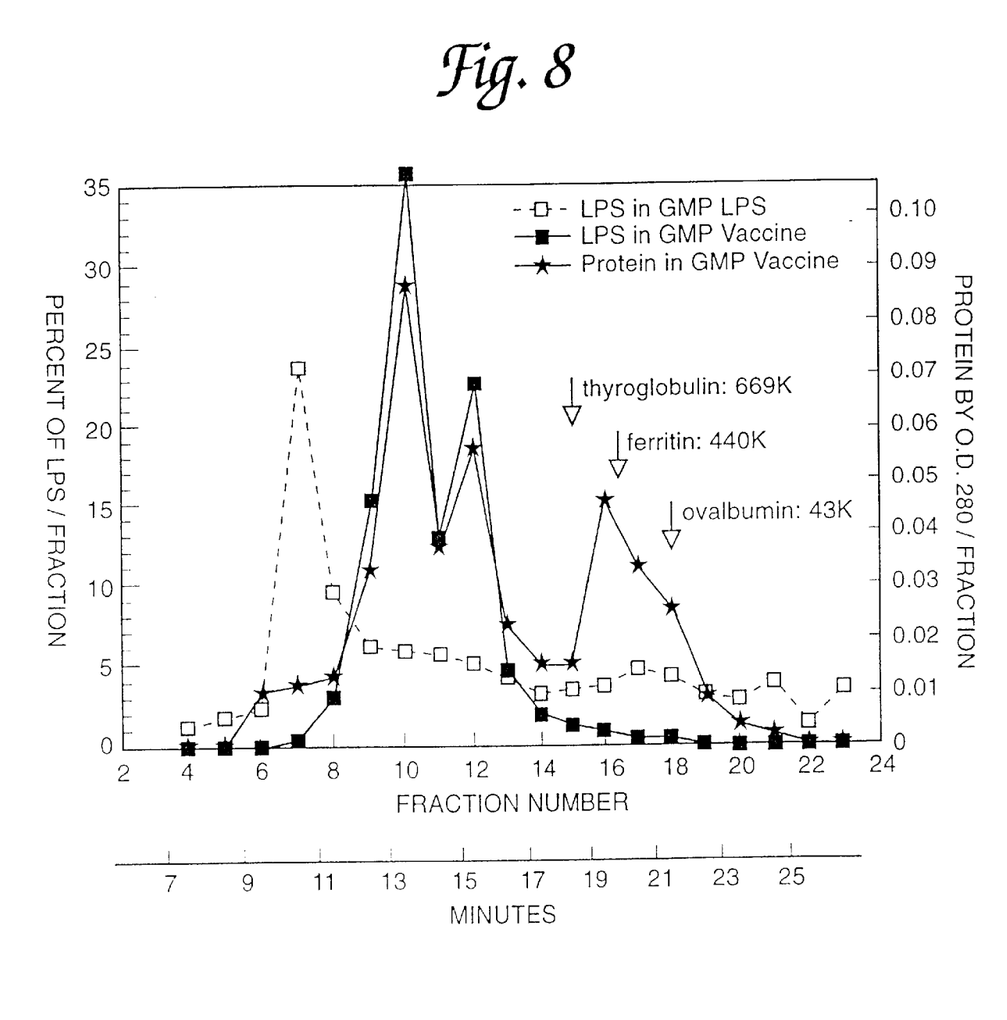
FIG. 8: LPS in HPLC fractions after applying uncomplexed *P. shigelloides* LPS and Demonstration of non-covalent complexing of LPS and proteosome proteins by co-elution of LPS and proteins in HPLC fractions after applying proteosome-*P. shigelloides* LPS vaccine.
Figure 9A:
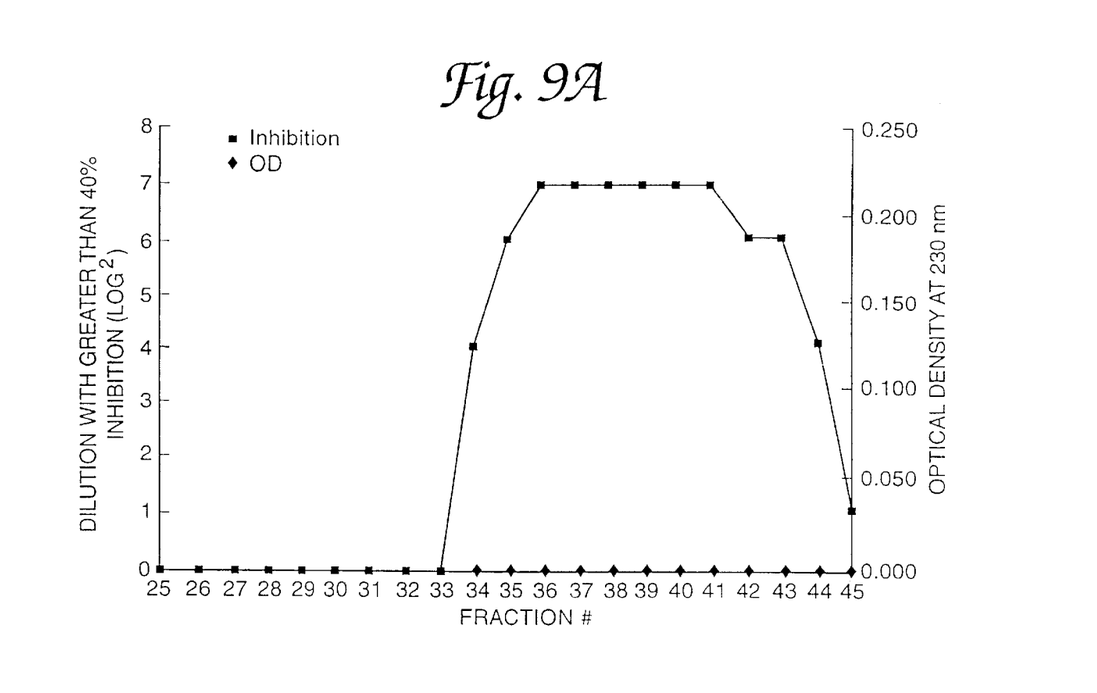
FIGS. 9A–B: Bactericidal antibody response of mice to meningococcal outer membrane protein-detoxified lipooligosaccharide vaccine, geometric mean reciprocal titers against meningococcal strain 9162
Figure 9B:
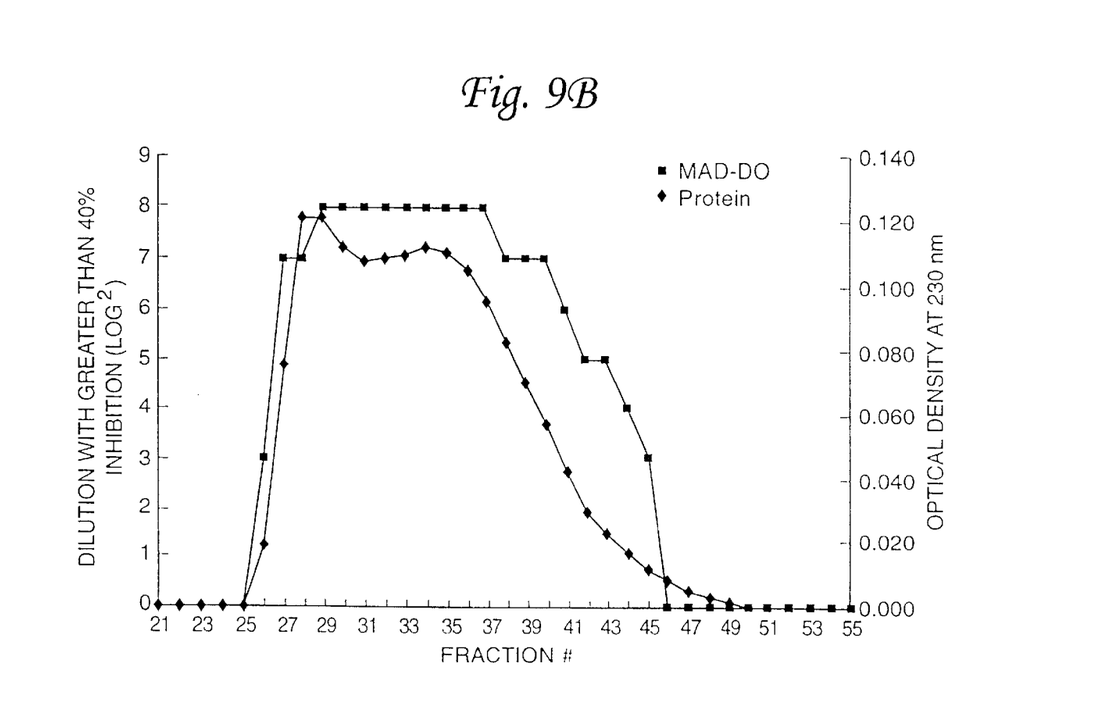

5.15 Demonstration of non-covalent complexing of the multimolecular proteosome proteins and LPS is shown in FIG. 8. The graph shows LPS in HPLC fractions after applying uncomplexed *P. shigelloides* LPS which occurs at a different part of the column elution profile than when applying the proteosome-LPS vaccine. The co-elution of LPS and proteins in HPLC fractions after applying proteosome-*P. shigelloides* LPS vaccine is shown with peaks that correspond to the largest protein aggregates of proteosomes. The data were measured using an inhibition ELISA to quantitate the LPS and using the OD at A280 to quantitate the proteosome proteins. The HPLC column was a Tosohaas G50000Pwxl and the molecular weight standards are indicated by the arrows.

What is claimed is:

1. A continuous process for the preparation of proteosome-amphiphilic determinant vaccine comprising
    a) forming a mixture of proteosome, a detergent and an amphiphilic determinant,
    b) continuously subjecting the mixture to a diafiltration or an ultrafiltration system to remove the detergent and form an amphiphilic determinant-proteosome complex in the retentate under non-static conditions,
    c) monitoring the amount of amphiphilic determinant-proteosome complex formation, and
    d) recovering the amphiphilic determinant-proteosome complex, wherein the nominal molecular weight cutoff of the system is about 3,000 or greater.

2. A process for the preparation of proteosome-amphiphilic determinant vaccine according to claim 1 wherein the ultrafiltration involves tangential flow.

3. A process for the preparation of proteosome-amphiphilic determinant vaccine according to claim 1 wherein the ultrafiltration system is selected from a hollow fiber cartridge, platform membrane and membrane cartridge.

4. A process for the preparation of proteosome-amphiphilic determinant vaccine according to claim 1 further comprising monitoring of the detergent by continual measuring of permeate samples.

5. A process for the preparation of proteosome-amphiphilic determinant vaccine according to claim 1 wherein monitoring includes measuring the optical density of permeate or retentate sample.

6. A process for the preparation of proteosome-amphiphilic determinant vaccine according to claim 1 wherein the monitoring involves measuring the amount of detergent removal by mixing a permeate sample with a known amount of SDS (sodium dodecyl sulfate) to form a precipitate if detergent is present, and determining the amount of precipitation.

7. A process for the preparation of proteosome-amphiphilic determinant vaccine according to claim 6 wherein the proteosome-amphiphilic determinant complex is recovered when the detergent in the permeate has been essentially removed.

8. A process for the preparation of proteosome-amphiphilic determinant vaccine according to claim 1 wherein the detergent is Empigen BB.

9. A process for the preparation of proteosome-amphiphilic determinant vaccine according to claim 1 wherein the amphiphilic determinant is a lipopolysaccharide.

10. A process for the preparation of proteosome-lipopolysaccharide vaccine according to claim 9 wherein the lipopolysaccharide is obtained from a gram negative bacteria.

11. A process for the preparation of proteosome-lipopolysaccharide vaccine according to claim 10 wherein the gram negative bacteria is a plesiomonas.

12. A process for the preparation of proteosome-lipopolysaccharide vaccine according to claim 11 wherein the plesiomonas is *Plesiomonas shigelloides*.

13. A process for the preparation of proteosome-lipopolysaccharide vaccine according to claim 10 wherein the gram negative bacteria is a shigella.

14. A process for the preparation of proteosome-lipopolysaccharide vaccine according to claim 13 wherein the shigella is *Shigella flexneri*, *Shigella sonnei*, or *Shigella boydii*.

15. A process for the preparation of proteosome-lipopolysaccharide vaccine according to claim 10 wherein the gram negative bacteria is a neisseria.

16. A process for the preparation of proteosome-lipopolysaccharide vaccine according to claim 15 wherein the neisseia is *Neisseria meningitidis*.

17. A process for the preparation of proteosome-amphiphilic determinant vaccine according to claim 1 wherein the proteosome is derived from *N. meningiditis* or *N. gonorrhea*.

18. A process for the preparation of proteosome-amphiphilic determinant vaccine according to claim 1 wherein the recovery of the LPS-proteosome complex is effected when the monitored rate of detergent removal is decreasing or constant.

19. A process for the preparation of proteosome-amphiphilic determinant vaccine according to claim 1 further comprising
 e) mixing the recovered proteosome-amphiphilic determinant complex with a physiologically acceptable carrier to form a vaccine.

20. A process for the preparation of proteosome-amphiphilic determinant vaccine according to claim 19 further comprising concentrating the proteosome-amphiphilic determinant complex prior to its recovery.

21. A process for the preparation of proteosome-amphiphilic determinant vaccine according to claim 20 wherein the concentration is continued to a desired final concentration.

22. A process for the preparation of proteosome-amphiphilic determinant vaccine according to claim 19 wherein the process is performed with different amphiphilic determinants types to form a series of proteosome-amphiphilic determinant complexes that are assembled in step e) to form a multivalent vaccine.

23. A multivalent vaccine prepared by the process of claim 22.

24. A process for protecting against a disease comprising administering the vaccine of claim 23 in an effective amount to a recipient.

25. A process for protecting against a disease comprising administering the vaccine prepared according to the process of claim 23 to a recipient.

* * * * *